`US009464045B2`

United States Patent
Koerfer et al.

(10) Patent No.: US 9,464,045 B2
(45) Date of Patent: Oct. 11, 2016

(54) PROCESS FOR THE PREPARATION OF METHIONINE

(71) Applicants: Martin Koerfer, Kahl (DE); Hans Joachim Hasselbach, Gelnhausen (DE); Stefan Reichert, Frankfurt (DE); Harald Jakob, Hasselroth (DE); Christoph Weckbecker, Gruendau (DE); Klaus Huthmacher, Gelnhausen (DE); Horst Krull, Hanau (DE); Bernd Drapal, Alzenau (DE); Rainer Peter, Krombach (DE)

(72) Inventors: Martin Koerfer, Kahl (DE); Hans Joachim Hasselbach, Gelnhausen (DE); Stefan Reichert, Frankfurt (DE); Harald Jakob, Hasselroth (DE); Christoph Weckbecker, Gruendau (DE); Klaus Huthmacher, Gelnhausen (DE); Horst Krull, Hanau (DE); Bernd Drapal, Alzenau (DE); Rainer Peter, Krombach (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/850,207

(22) Filed: Sep. 10, 2015

(65) Prior Publication Data
US 2016/0068480 A1    Mar. 10, 2016

Related U.S. Application Data

(63) Continuation of application No. 14/386,165, filed as application No. PCT/EP2013/053795 on Feb. 26, 2013, now Pat. No. 9,156,782.

(30) Foreign Application Priority Data

Mar. 20, 2012   (EP) .................................... 12160257

(51) Int. Cl.
| C07C 319/28 | (2006.01) |
| C07C 319/20 | (2006.01) |
| C07C 319/26 | (2006.01) |
| C07C 319/12 | (2006.01) |
| C07C 323/52 | (2006.01) |

(52) U.S. Cl.
CPC .......... *C07C 319/28* (2013.01); *C07C 319/12* (2013.01); *C07C 319/20* (2013.01); *C07C 319/26* (2013.01); *C07C 323/52* (2013.01); *Y02P 20/142* (2015.11)

(58) Field of Classification Search
None
See application file for complete search history.

(56) References Cited

U.S. PATENT DOCUMENTS

| 2005/0131111 A1* | 6/2005 | Weckbecker ......... C07C 319/20 524/35 |
| 2012/0178966 A1* | 7/2012 | Hong ........................ C05C 3/00 562/559 |

FOREIGN PATENT DOCUMENTS

| JP | 46019610 | 1/1971 |
| JP | 11-158140 | 6/1999 |
| JP | 2004-292324 | 10/2004 |
| WO | 03/050071 A1 | 6/2003 |
| WO | WO 03/050071 A1 | 6/2003 |

OTHER PUBLICATIONS

International Search Report issued Apr. 19, 2013, in PCT/EP13/53795 filed Feb. 26, 2013.
Written Opinion of the International Searching Authority issued Apr. 19, 2013, in PCT/EP13/53795 filed Feb. 26, 2013.

* cited by examiner

*Primary Examiner* — Yevegeny Valenrod
(74) *Attorney, Agent, or Firm* — Oblon, McClelland, Maier & Neustadt, L.L.P.

(57) ABSTRACT

This disclosure relates to a process for preparing D,L-methionine by feeding carbon dioxide to an aqueous potassium methioninate solution obtained by hydrolysis of 5-(2-methylmercaptoethyl)hydantoin, in order to precipitate out crude methionine, which is separated off and purified. In this process an aqueous solution of the separated-off crude methionine is purified by recrystallization from a solution containing potassium ions and also a crystallization additive. The crystallization additive is a nonionic or anionic surfactant, or a mixture of different nonionic or anionic surfactants. The recrystallization occurs by introducing a 60 to 110° C.-hot methionine solution into a 35 to 80° C.-warm methionine suspension, a temperature of which is lower than that of the introduced solution, such that the temperature of the methionine suspension being maintained between 35 and 80° C. during the addition. The crystallization additive is a sorbitan fatty acid ester or a mixture of different sorbitan fatty acid esters.

12 Claims, 4 Drawing Sheets

PROCESS FOR THE PREPARATION OF METHIONINE

CROSS-REFERENCE TO RELATED APPLICATIONS

This application is a Continuation of U.S. Non-Provisional application Ser. No. 14/386,165, which was filed on Sep. 18, 2014. Application Ser. No. 14/386,165 is a National Stage of PCT/EP2013/053795, which was filed on Feb. 26, 2013. This application is based upon and claims the benefit of priority to European Application No. 12160257.7, which was filed on Mar. 20, 2012.

BACKGROUND OF THE INVENTION

The invention relates to a process for the preparation of D,L-methionine with a high bulk density, where the methionine is purified by recrystallization.

L-Methionine is an essential amino acid which is of great industrial importance as a feed supplement. Since D- and L-methionine are of identical nutritional value, the racemate is usually used as feed supplement. The synthesis of D,L-methionine proceeds starting from methylmercaptopropionaldehyde and hydrogen cyanide with the preparation of the intermediate 5-(2-methylmercaptoethyl)hydantoin, which can be converted to the methioninate by hydrolysis.

Various processes are known both for the hydrolysis of hydantoin and also for the subsequent release of methionine from its salt. The present invention relates to the preparation of methionine by the so-called potassium carbonate process, which is described for example in EP 1 256 571 A1 and DE 19 06 405 A1. In this connection, 5-(2-methylmercaptoethyl)hydantoin in aqueous solution is firstly reacted with potassium carbonate to give potassium methioninate with the release of carbon dioxide and ammonia. By introducing carbon dioxide, the basic potassium methioninate solution is neutralized and methionine is precipitated out. The crude methionine obtained in this way, however, is produced in the form of platelet-like or flake-like, poorly filterable crystals, which are shown in FIG. 1.

To control the foaming and to improve the crystal quality, the crude methionine precipitation according to EP 1 256 571 A1 takes place in the presence of an antifoam. This process has the disadvantage that methionine is obtained in the form of spherical, but porous particles, which are shown in FIG. 2. Because of its porous structure, the methionine obtained in such a way has to be washed with large amounts of water and dried, incurring high energy costs, in order to arrive at a marketable product.

The addition of additives during the crude methionine precipitation can improve the crystal quality. As additives, for example sorbitan laurate, polyvinyl alcohol, hydroxypropylmethylcellulose, gluten or casein are known from JP 11158140 and JP 10306071. According to these processes, methionine crystals with a bulk density of up to 770 g/l are obtained. It has proven to be disadvantageous for these processes that they are carried out as batch processes or in merely semicontinuous mode.

It is likewise known to improve purity and bulk density of methionine by recrystallization of crude methionine. JP 2004-292324 discloses, for example, the recrystallization of crude methionine by adding polyvinyl alcohol or gluten, giving pure methionine with a bulk density of up to 580 g/l. The recrystallization takes place by the dropwise addition of a hot methionine solution to a cold methionine suspension, with methionine precipitating out as a result of cooling the hot solution. A disadvantage has again proven to be that this process is not carried out continuously.

EP 1 451 139 A1 describes the recrystallization of methionine in the presence of hydroxyethylcellulose, with initially methionine crystals having a bulk density of up to 620 g/l being obtained. In this case, a disadvantage has proven to be that in a continuous recrystallization process there is an accumulation of the continuously added additive as a result of reusing the filtrate for dissolving crude methionine and that an increasing additive concentration results in a reduction in the bulk density. For this reason, hydroxyethylcellulose is not advantageous for use as crystallization additive in a continuous process in which the filtrate of the pure methionine is reused for dissolving crude methionine. The reuse of the recrystallization filtrate is of decisive importance for the economic feasibility of the process on an industrial scale since losses of dissolved methionine are avoided and the generation of wastewater is minimized.

JP 46 019610 B1 describes a process for the recrystallization of methionine, which however does not allow to achieve high bulk densities for methionine.

It is an object of the present invention to provide a process for the preparation of methionine which avoids the described disadvantages. The methionine obtained by the process should be readily filterable and have a high bulk density. Furthermore, the process should be able to be carried out in continuous mode and in particular should avoid the negative consequences of accumulation processes.

BRIEF SUMMARY OF THE INVENTION

To achieve this object, the present invention provides a process for the preparation of D,L-methionine, in which carbon dioxide is fed to an aqueous potassium methioninate solution obtained by hydrolysis of 5-(2-methylmercaptoethyl)hydantoin, in order to precipitate out crude methionine, which is separated off and purified, where, for the purposes of purification, an aqueous solution of the separated-off crude methionine is prepared and subjected to a recrystallization. In the process, the solution from which the recrystallization takes place contains potassium ions and also a crystallization additive, where the crystallization additive is a nonionic or anionic surfactant, or a mixture of different nonionic or anionic surfactants. According to the invention, the recrystallization takes place by introducing a 60 to 110° C.-hot methionine solution into a 35 to 80° C.-warm methionine suspension, the temperature of which is lower than that of the introduced solution, the temperature of the methionine suspension being maintained between 35 and 80° C. during the addition.

The hot methionine solution is preferably cooled rapidly by introducing it into the initial charge of cooler methionine suspension, as a result of which a superconcentration of dissolved methionine is produced and methionine precipitates out from the solution. In this way, the preference in the crystal growth spatial direction is interrupted and an isometric crystal habit is achieved. However, besides the desired isometric crystals, it is also possible for undesired new, platelet-like crystal germs to form as a result of this rapid cooling mode. In one preferred embodiment of the process according to the invention, these can be specifically redissolved by moderately increasing the temperature by 5-15° C., preferably by 6-12° C., compared to the mixing temperature.

As a result of the combination according to the invention of the presence of potassium ions, the addition of crystallization additive and the temperature control of the recrystallization, coarsely granular, readily filterable methionine crystals with a bulk density of above 500 g/l are obtained.

DETAILED DESCRIPTION OF THE INVENTION

Figure 1:
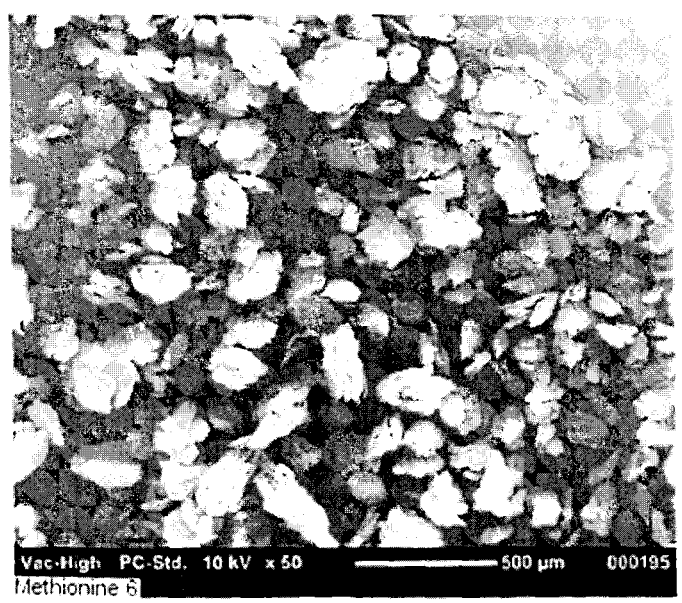
FIG. 1 illustrates a crude methionine produced in the form of platelet-like or flake-like, poorly filterable crystals.

In a preferred embodiment of the process, the crystallization additive is one of the compounds shown in formulae 1 to 3, or a mixture thereof:

$R^1$—O—$SO_3$M     (formula 1)

$R^2$—O—$(CH_2)_n$—$SO_3$M     (formula 2)

$R^3$—(O—$C_2H_4)_n$—O—$SO_3$M     (formula 3)

where n is an integer from 1 to 12, M is sodium or potassium and $R^1$, $R^2$ and $R^3$ are a linear, branched or cyclic, saturated or unsaturated $C_8$ to $C_{20}$ alkyl group or an aryl group.

In a preferred embodiment of the aforementioned compounds, n=2 and $R^1$, $R^2$ and $R^3$ are linear, saturated $C_8$ to $C_{18}$ alkyl groups.

In a further embodiment of the process, the crystallization additive is a sorbitan fatty acid ester or a mixture of different sorbitan fatty acid esters, preferably polyethoxylated sorbitan fatty acid esters. In a particularly preferred embodiment, the crystallization additive is a polyethoxylated sorbitan stearate, and in particular a polyethoxylated sorbitan tristearate according to formula 4:

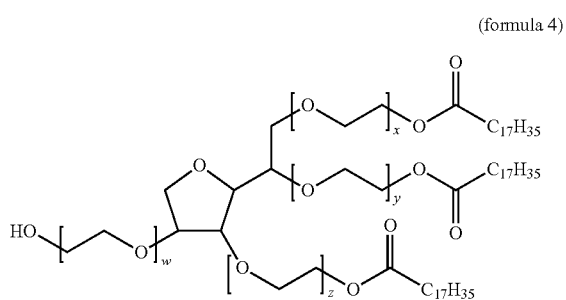

(formula 4)

where w+x+y+z=20.

The concentration of the crystallization additive in the solution from which the recrystallization takes place is preferably at least 50 ppm based on the total mass of the solution, particularly preferably at least 100 ppm, most preferably at least 400 ppm. In order to achieve an optimum dosing and distribution of the crystallization additive, it is preferably used in the form of an aqueous solution or emulsion, in which case the concentration of the crystallization additive in the solution or emulsion is preferably 2 to 15% by weight.

In a preferred embodiment of the process according to the invention, the solution from which the recrystallization takes place additionally comprises an antifoam. The antifoam has the function of suppressing the foam which is formed when handling the methionine solution and suspension and which is intensified and/or caused by some of the aforementioned crystallization additives. Moreover, a synergistic effect arises for the attained bulk densities of methionine when simultaneously using antifoam and crystallization additives, as a result of which bulk densities of more than 600 g/l are achieved, the negative consequences of accumulation processes are simultaneously avoided and the process according to the invention can thus also be carried out in continuous mode.

The antifoam preferably comprises silicone oil, preference being given to using a silicone oil with a kinematic viscosity of 0.65 to 10 000 $mm^2$/s (measured at 25° C. in accordance with DIN 53018), particularly preferably from 90 to 1500 $mm^2$/s. The antifoam can further contain constituents which are effective as emulsifiers, for example mixtures of polyethoxylated fatty acids and polyethoxylated fatty alcohols. The antifoam can likewise comprise silica. In a preferred embodiment, the antifoam is an aqueous solution which comprises 5 to 10% by weight of silicone oil, 0.05 to 1% by weight of silica, 0.5 to 5% by weight of a mixture of polyethoxylated fatty acids, and 2 to 7% by weight of a mixture of polyethoxylated fatty alcohols. Preferably, the antifoam is used in a mixture with the crystallization additive, the crystallization additive being admixed in a concentration of preferably 2 to 15% by weight. In order to achieve a continuous, stable dosing of the antifoam, it is preferably further diluted with water prior to being used.

The use of silicone oil antifoams leads to silicon being able to be detected in the methionine prepared by the process according to the invention using a suitable analysis method (e.g. X-ray photoelectron spectroscopy, abbreviated to XPS). Therefore, a further object of the present invention is D,L-methionine obtained by the process according to the present invention, wherein a silicone oil antifoam is used in said process.

Surprisingly, it has been found that the presence of potassium ions in the solution from which the recrystallization takes place is important for the crystallization success. Preferably, the potassium ion concentration in the solution from which the recrystallization takes place is 1 to 30 g/kg, particularly preferably 2 to 14 g/kg, most preferably 5 to 10 g/kg. The potassium preferably passes into the recrystallization solution with the crude methionine. The potassium concentration can be adjusted for example by introducing washing water during the crude methionine filtration and/or by introducing freshwater to the pure filtrate used for dissolving the crude methionine and/or by introducing potassium into the pure filtrate used for dissolving the crude methionine.

According to the invention, the crude methionine is dissolved in an aqueous solution before the recrystallization. This is effected preferably by heating the solution to a temperature of at least 95° C., particularly preferably by heating to boiling temperature. To dissolve the crude methionine, it is possible to use, for example, freshwater, the filtrate of the pure methionine, or the condensate of the vacuum crystallization described below or mixtures thereof.

According to the invention, crystallization additive and the antifoam are added to the aqueous matrix used for dissolving the crude methionine. In one possible embodiment of the process, the crystallization additive and the antifoam are also added to the solution from which the crude methionine is precipitated out.

Preferably, the recrystallization takes place by introducing an 85 to 110° C.-hot crude methionine solution into a 35 to 60° C.-warm methionine suspension, the temperature of the mixture that is formed as a result being kept constant between 35 and 60° C. In this connection, the volume ratio of the introduced crude methionine solution to the initial charge of methionine suspension is preferably in the range from 1:1 to 1:10, particularly preferably from 1:3 to 1:6.

In a further preferred embodiment of the process, the recrystallization is carried out in two stages. For this, in the first recrystallization stage, an 85 to 110° C.-hot crude methionine solution is introduced into a 60 to 80° C.-warm methionine suspension and the temperature of the mixture that is formed as a result is kept constant between 60 and 80° C. It is particularly preferred here to remove some of the methionine suspension from the first recrystallization stage and to return it again to the recrystallization via a circulation circuit, the temperature of the suspension in the circulation circuit being increased by 6 to 12° C. The 60 to 80° C.-warm methionine suspension obtained in the first recrystallization stage is introduced, in a second recrystallization stage, into a 35 to 60° C.-warm methionine suspension, the temperature of the mixture that is formed as a result being kept constant between 35 and 60° C. The volume ratio of the introduced methionine suspension to the initial charge of methionine suspension is preferably in the range from 1:1 to 1:10, particularly preferably from 1:3 to 1:6.

Besides a first or a first and second recrystallization stage, the process according to the invention can also involve further recrystallization stages.

In the event of a multistage procedure, all stages can be charged in parallel with crude methionine at the same temperature difference between crude methionine solution and initial charge of methionine suspension. The multistage recrystallization can also be carried out such that the recrystallization stages are successively charged with the methionine solution from the proceeding stage, the temperature difference between crude methionine and methionine solution being selected such that the methionine solution from one recrystallization stage can be used as crude methionine for the next recrystallization stage. This has the advantage of reduced formation of undesired platelet-like crystals as a result of excessively large temperature differences. The multistage recrystallization of course also involves mixed forms of parallel and consecutive charging of the recrystallization units.

Figure 6:
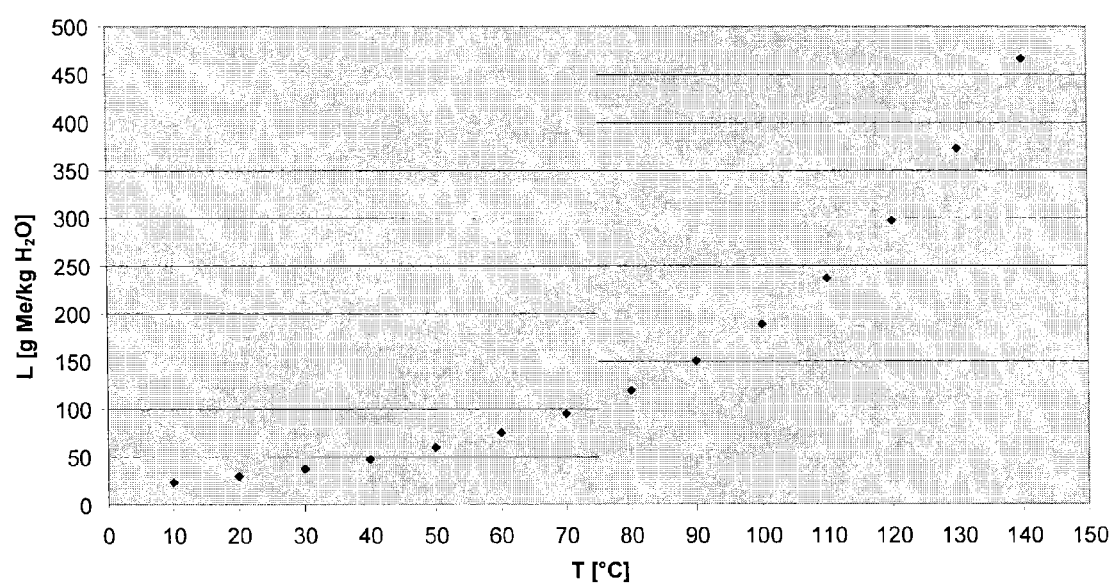
FIG. 6 shows a graph of the temperature-dependent solubility behaviour of methionine.

The preferred temperature control for the process according to the invention arises from the temperature-dependent solubility behaviour of methionine shown in FIG. 6.

In economic terms, it is expedient to cool the methionine solutions to an end temperature of from 30 to 50° C. since, in so doing, both the amount of methionine remaining in solution can be minimized, and also the use of expensive cooling media for the purposes of further cooling the methionine-containing solutions is avoided.

In a preferred embodiment of the process, the recrystallization is carried out by vacuum crystallization. Here, the pressure in the first recrystallization stage is preferably 100 to 1000 mbar, particularly preferably 150 to 400 mbar. If a two-stage recrystallization is carried out, the pressure in the second recrystallization stage is preferably 35 to 200 mbar, particularly preferably 35 to 100 mbar. Preferably, the water evaporated in the vacuum crystallization is condensed and is reused for dissolving further crude methionine.

In one preferred embodiment of the process, some of the methionine suspension is removed from the first and/or one of the other recrystallization stages and is returned again via a circulation circuit. In the first crystallization stage, the hot methionine solution is preferably added to the circulated colder suspension in a volume ratio of 1:3 to 1:6. Upon this rapid cooling, a high supersaturation is produced, as a result of which, on the one hand, relatively large crystals grow isometrically, or else new, small, platelet-like crystals are formed. The small platelet-like crystals are also dissolved again in the recirculation line by increasing the temperature by 6 to 12° C., the isometric relatively large crystals being retained.

Separating off the pure methionine from the mother liquor of the recrystallization preferably takes place by filtration, for example pressure or vacuum filtration, or by means of centrifuges, for example trailing-blade, pusher-type or screen centrifuges.

The process according to the invention can either be carried out continuously or else discontinuously or semi-continuously.

Figure 2:
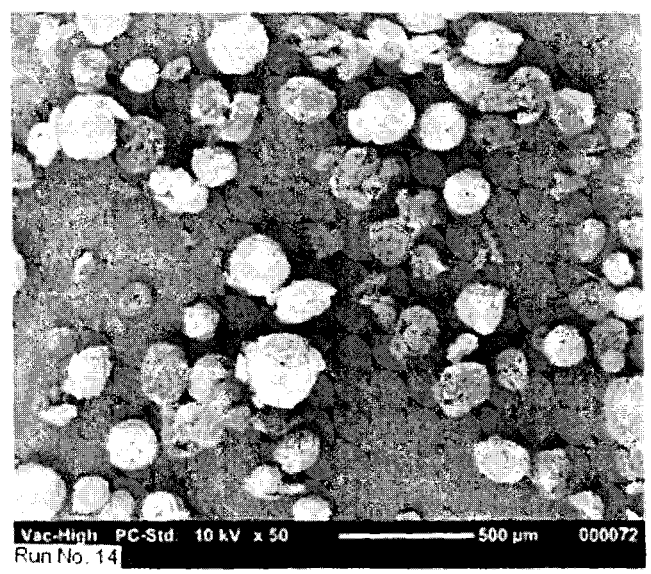
FIG. 2 illustrates a crude methionine produced in the form of spherical, but porous particles.
Figure 3:
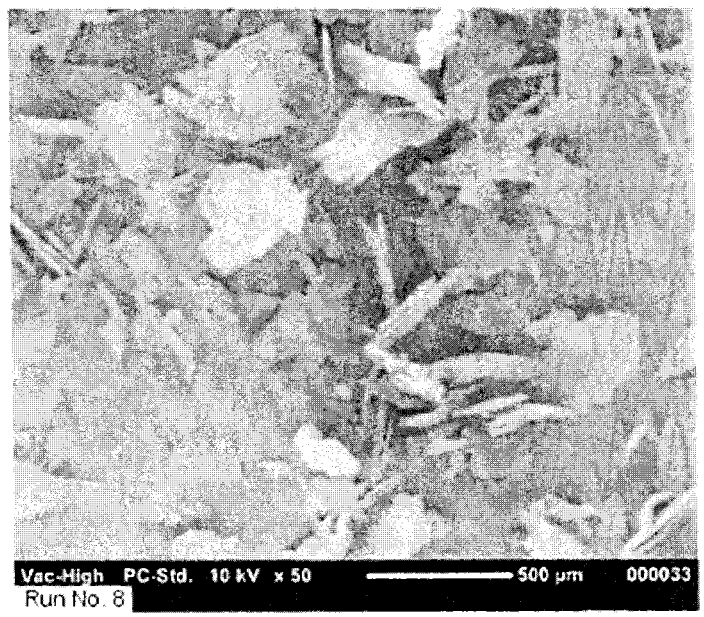
FIG. 3 illustrates methionine obtained without the addition of crystallization additives, without the presence of potassium by simple cooling.
Figure 4:
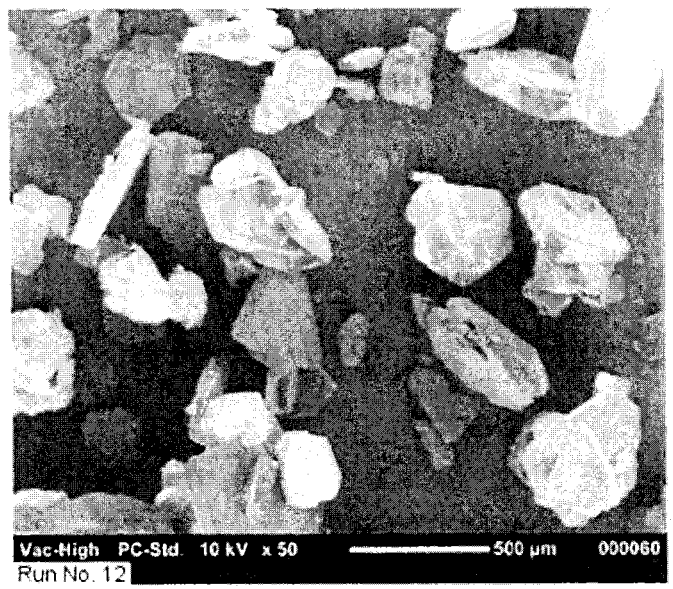
FIG. 4 illustrates a pure methionine according to one embodiment of the present disclosure.

The attached FIGS. 1 to 4 show electron micrographs of crystalline methionine. FIG. 1 shows crude methionine as is obtained from the crude methionine precipitation without the addition of crystallization additives. FIG. 2 shows crude methionine from the crude methionine precipitation with the addition of an antifoam according to EP 1 256 571 A1. FIG. 3 shows methionine as is obtained without the addition of crystallization additives, without the presence of potassium by simple cooling. FIG. 4 shows pure methionine as is obtained with the process according to the invention.

Figure 5:
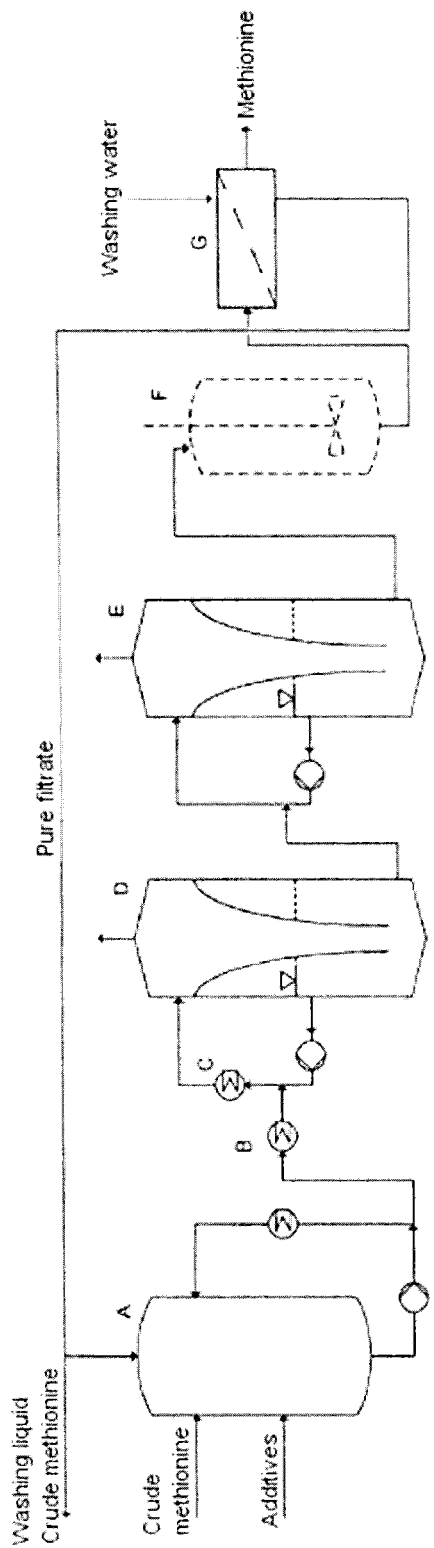
FIG. 5 illustrates an arrangement, in diagrammatic form, for carrying out a process according to one embodiment of the present disclosure.

FIG. 5 shows, by way of example and in diagrammatic form, an arrangement for carrying out the process according to the invention in a preferred two-stage recrystallization. In container A, crude methionine is dissolved with an aqueous matrix, which can comprise the filtrate of the pure methionine, at a temperature of from 90 to 100° C. The temperature is adjusted via a circulation pump and an external heat exchanger. The crystallization additive according to the invention including antifoam is added continuously to the aqueous matrix. The methionine solution is heated to 100 to 110° C. via one or more heat exchangers B and then fed to the circulation circuit of the first vacuum crystallizer D. The circulated suspension has a temperature of 60 to 70° C. The ratio of amount fed in to circulation amount is in the range from 1:3 to 1:6. The average residence time of the mixture in the circulation circuit is 5 to 15 sec. The mixture is heated to 65 to 75° C. via a heat exchanger C, as a result of which fine and in particular platelet-like methionine crystals rapidly dissolve because of their relatively large specific surface area. The mixture then passes to the first vacuum crystallizer D, in the top region of which, at a pressure of 180 to 200 mbar, water evaporation and cooling of the mixture occurs. This results in crystallization of dissolved methionine. The methionine crystals settle out in the vacuum crystallizer at differing rates. Small, platelet-like crystals settle out more slowly than coarse, isometric crystals. The suspension for recirculation is removed in the upper region of the vacuum crystallizer, where predominantly smaller, platelet-like crystals are found on account of the slower settling rate. The coarse, isometric crystals are removed in the lower region of the vacuum crystallizer D and fed to the circulation circuit of the second vacuum crystallizer E. The suspension circulated here has a temperature of 30 to 50° C. The ratio of amount fed in to circulation amount is in the range from 1:3 to 1:6. The pressure in the vacuum crystallizer E is 60 to 80 mbar. In vacuum crystallizer E, further methionine is crystallized, as a result of which the average particle size of the methionine crystals in particular is increased. If required, the methionine suspension can be passed to an interim container F in order to permit a postprecipitation of methionine. Finally, the methionine is isolated in a suitable solid/liquid separation step G, where the filtrate obtained can, if required, be returned to container A.

The examples below aim to explain the invention in more detail.

EXAMPLES

Example 1

Recrystallization in the Presence of a Crystallization Additive According to the Invention Compared with a Known Crystallization Additive 60 g of methionine, 305 g of water and 35 g of crude methionine filtrate were introduced into a flask and circulated via a heat exchanger by pumping at a temperature of 40° C. As a result of the potassium carbonate present in the crude methionine filtrate, the potassium ion concentration was ca. 7 g/kg. A solution, heated to 90° C., of 150 g of methionine in 990.5 ml of water and 109.5 g of crude methionine filtrate was added to this suspension at a rate of 18 ml/min, during which the temperature of the initial charge of suspension was kept at 40° C. After adding 650 ml of the hot solution, 500 ml of suspension were removed and then a further 500 ml of the hot solution were metered in at a rate of 18 ml/min. The resulting suspension was discharged, the amount of foam was determined, and the methionine was filtered off and washed with 300 ml of acetone. After drying the methionine, the bulk density was determined.

The recrystallization experiments were carried out in the presence of the following additives, the stated concentration being established by adding the additive to both starting solutions/suspensions. The concentration data give the total active ingredient content of the additive without water based on the total mass of the solution or suspension. Additive 1 was an aqueous mixture of antifoam and crystallization additive according to EP 1 451 139 A1, consisting of 2% by weight of hydroxyethylcellulose and 2% by weight of a polyethoxylated fatty acid ($C_{18}H_{37}$—(CO)—O—($CH_2$—$CH_2O$)$_7$—H). Additive 2 was an aqueous mixture of a crystallization additive and an antifoam composition according to the present invention, consisting of 6.1% by weight of silicone oil with a kinematic viscosity of 1000 mm²/s (AK 1000, Wacker-Chemie GmbH), 0.25% by weight of hydrophobicized silica (Sipernat D10, Evonik Degussa GmbH), 2.6% by weight of a polyethoxylated fatty acid mixture (Intrasol® FS 18/90/7, Ashland Deutschland GmbH), 3.7% by weight of a polyethoxylated fatty alcohol mixture (2.35% by weight of Marlipal®, Sasol Germany GmbH, 1.35% by weight of Brij C2, Croda Chemicals Europe) and 5.1% by weight of a fatty alcohol sulphate (Sulfopon® 1218 G, Oleochemicals) according to the formula:

$C_nH_{2n+1}$—O—$SO_3Na$, where n=12 to 18.

The table below shows the ascertained amounts of foam and methionine bulk densities as a function of type and concentration of the mixtures used as crystallization additives, the total active ingredient content (without water) being given.

| Additive | Concentration (ppm) | Amount of foam (ml) | Bulk density (g/l) |
|---|---|---|---|
| None | — | 300 | 507 |
| 1 | 200 | 180 | 614 |
| 1 | 400 | 75 | 626 |
| 1 | 1000 | 10 | 587 |
| 1 | 1200 | 10 | 464 |
| 1 | 2000 | 10 | 410 |
| 1 | 4000 | 5 | 356 |
| 2 | 200 | 40 | 613 |
| 2 | 400 | 5 | 633 |
| 2 | 1000 | 0 | 610 |
| 2 | 1200 | 0 | 651 |
| 2 | 2000 | 0 | 625 |
| 2 | 4000 | 0 | 639 |

It is observed that the crystallization additive according to the invention at a low concentration improves the bulk density as effectively as the additive according to EP 1 451 139 A1 and that the additive according to the invention, in contrast to the additive according to EP 1 451 139 A1, retains its effectiveness even at a high concentration.

Example 2

Recrystallization in the Presence of Pure Antifoam, Pure Crystallization Additives, and Mixtures of Antifoam and Crystallization Additive Recrystallization experiments according to the procedure from Example 1 were carried out with the addition of pure crystallization additives according to the invention, of mixtures of the crystallization additives with the antifoam and of the pure antifoam. The table below shows the amounts of foam and methionine bulk densities ascertained here.

The pure antifoam (Comparative Example 1) was used in the form of an aqueous mixture consisting of 6.1% by weight of silicone oil with a kinematic viscosity of 1000 mm²/s (AK 1000, Wacker-Chemie GmbH), 0.25% by weight of hydrophobicized silica (Sipernat D10, Evonik Degussa GmbH), 2.6% by weight of a polyethoxylated fatty acid mixture (Intrasol® FS 18/90/7, Ashland Deutschland GmbH), 3.7% by weight of a polyethoxylated fatty alcohol mixture (2.35% by weight of Marlipal®, Sasol Germany GmbH, 1.35% by weight of Brij C2, Croda Chemicals Europe).

The pure crystallization additives used were the following anionic surfactants:

2) $C_nH_{2n+1}$—O—$SO_3Na$, where n=12 to 18 (Sulfopon® 1218G, Oleochemicals)

3) $C_nH_{2n+1}$—O—$C_2H_4$—$SO_3Na$, where n=8 to 18 (Hostapon® SCI 85, Clariant)

4) $C_nH_{2n+1}$—$(OC_2H_4)_2$—O—$SO_3Na$, where n=12 (Disponil® FES 27, Cognis)

5) $C_nH_{2n+1}$—$(OC_2H_4)_{12}$—O—$SO_3Na$, where n=12 (Disponil® FES 993, Cognis)

Comparative Example 6) $C_nH_{2n+1}$—$(OC_2H_4)_{30}$—O—$SO_3Na$, where n=12 (Disponil® FES 77, Cognis)

For the mixtures of the antifoam with the crystallization additives, in each case 5.1% by weight of the corresponding crystallization additive was added to the aforementioned mixture and the water fraction was reduced by 5.1% by weight of:

7) (1)+(2)
8) (1)+(3)
9) (1)+(4)
10) (1)+(5)
Comparative Example 11) (1)+(6)

| Additive | Concentration (ppm) | Amount of foam (ml) | Bulk density (g/l) |
|---|---|---|---|
| Comparative Example 1 | 400 | 70 | 474 |
| 2 | 400 | 30-40 | 537 |
| 3 | 400 | 160 | 564 |
| 4 | 400 | >300 | 560 |
| 5 | 400 | >300 | 558 |
| Comparative Example 6 | 400 | >400 | 528 |
| 7 | 400 | 5 | 633 |
| 8 | 400 | 5 | 624 |
| 9 | 400 | 20-30 | 613 |
| 10 | 400 | 40 | 581 |
| Comparative Example 11 | 400 | 60 | 548 |

The results show that the pure antifoam does not result in an improvement in bulk density (entry 1). The crystallization additives 2 to 5 according to the invention improve the bulk density to values >500 g/l, but in the majority of cases bring about increased foaming. The combinations 7 to 9 according to the invention of antifoam and crystallization additives lead to bulk densities >600 g/l, the combination 10 according to the invention leads to bulk densities >500 g/l, without increased foaming arising.

Example 3

Recrystallization in the Presence of Antifoam and Crystallization Additives or Antifoam and Mixtures of Crystallization additives Further recrystallization experiments according to the procedure from Example 1 were carried out with mixtures of a antifoam and a crystallization additive or mixtures of an antifoam and several crystallization additives. For this purpose, the following mixtures were used:

8) (1)+(3) in concentrations of 200, 400, 1200, 2000 and 4000 ppm 9) (1)+(4) in concentrations of 200, 400, 1000, 1200, 2000 and 4000 ppm 10) (1)+(5) in concentrations of 200, 400, 1000, 1200, 2000 and 4000 ppm 11) (1)+((3)+(2) at the ratio of 1:1) in concentrations of 200, 400, 1200, 2000 and 4000 ppm 12) (1)+((4)+(2) at the ratio of 1:2) in concentrations of 200, 400, 1200, 2000 and 4000 ppm

| Additive | Concentration (ppm) | Amount of foam (ml) | Bulk density (g/l) |
|---|---|---|---|
| 8 | 200 | 70 | 599 |
| 8 | 400 | 0 | 624 |
| 8 | 1200 | 0 | 616 |
| 8 | 2000 | 0 | 610 |
| 8 | 4000 | 0 | 610 |

| Additive | Concentration (ppm) | Amount of foam (ml) | Bulk density (g/l) |
|---|---|---|---|
| 9 | 200 | 60 | 598 |
| 9 | 400 | 40 | 607 |
| 9 | 1000 | 0 | 600 |
| 9 | 1200 | 0 | 612 |
| 9 | 2000 | 0 | 594 |
| 9 | 4000 | 0 | 584 |

| Additive | Concentration (ppm) | Amount of foam (ml) | Bulk density (g/l) |
|---|---|---|---|
| 10 | 200 | 280 | 551 |
| 10 | 400 | 40 | 581 |
| 10 | 1000 | 20 | 579 |
| 10 | 1200 | 5 | 544 |
| 10 | 2000 | 5 | 545 |
| 10 | 4000 | 5 | 531 |

| Additive | Concentration (ppm) | Amount of foam (ml) | Bulk density (g/l) |
|---|---|---|---|
| 11 | 200 | 40 | 628 |
| 11 | 400 | 0 | 640 |
| 11 | 1200 | 0 | 624 |
| 11 | 2000 | 0 | 614 |
| 11 | 4000 | 0 | 612 |

| Additive | Concentration (ppm) | Amount of foam (ml) | Bulk density (g/l) |
|---|---|---|---|
| 12 | 200 | 60 | 602 |
| 12 | 400 | 20 | 605 |
| 12 | 1200 | 0 | 628 |
| 12 | 2000 | 0 | 625 |
| 12 | 4000 | 0 | 621 |

The results summarized in the tables above show that—in contrast to the process described in EP 1 451 139 A1—an increase in the concentration of the tested additives does not lead to a decrease in bulk density or at least not to a significant decrease in bulk density.

Comparative Example 1

Recrystallization in the Presence of Anionic Surfactants

Recrystallization experiments were carried out with the anionic surfactants (13) sodium dodecylbenzenesulfonate and (14) dioctyl sodium sulfosuccinate known from JP 46 019610 B. Here, the pure surfactants were used in a concentration of 400 ppm each.

| Additive | Concentration (ppm) | Amount of foam (ml) | Bulk density (g/l) |
|---|---|---|---|
| 13 | 400 | >400 | 348 |
| 14 | 400 | 0 | 446 |

The experimental data show that these surfactants lead to results which are worse than the results for the surfactants tested in Example 2.

Example 4

Recrystallization in the Presence of Nonionic Surfactants

Recrystallization experiments according to the procedure from Example 1 were carried out with the addition of nonionic surfactants. The following sorbitan based surfactants were used in the recrystallization experiments, where the surfactants were each used in a concentration of 400 ppm.

15) Tego SMO V; sorbitan monooleate (PET10-084)
16) Tego STO V; sorbitan trioleate (PET10-086)
17) Tego SMS 60; polyethoxylated sorbitan monostearate (Pet 10-087)
18) Tego SMS; sorbitan monostearate (Pet 10-088)
19) Span 60; sorbitan monostearate (Pet 10-095)
20) Span 80; sorbitan monooleate (Pet10-096)
21) Span 83; sorbitan sesquioleate (Pet10-097)
22) Span 65; sorbitan tristearate (Pet12-167)
23) Tween 61; polyethoxylated (4 EO) sorbitan tristearate (Pet12-169)
24) Tween 65; polyethoxylated (20 EO) sorbitan tristearate (Pet10-089)

| Additive | Concentration (ppm) | Amount of foam (ml) | Bulk density (g/l) |
|---|---|---|---|
| 15 | 400 | 0 | 356 |
| 16 | 400 | 0 | 483 |
| 17 | 400 | 320 | 526 |
| 18 | 400 | 0-5 | 346 |
| 19 | 400 | 0-5 | 345 |
| 20 | 400 | 0 | 335 |
| 21 | 400 | 0 | 356 |
| 22 | 400 | 60 | 446 |
| 23 | 400 | 20 | 499 |
| 24 | 400 | 0 | 616 |

With the non-ionic surfactant polyethoxylated sorbitan monostearate (Tween™ 65 from Croda) in a concentration of 400 ppm a methionine bulk density of 616 g/l was achieved.

Example 5

Influence of the Potassium Ion Concentration on the Bulk Density of Methionine 1000 g of a 95° C.-hot solution of 100 g of methionine in 900 g of water were added dropwise, with stirring, to a 40° C.-warm suspension of 20 g of methionine in 180 g of water over 2 h, during which the temperature of the initial charge of suspension was kept at 40° C. The experiments were carried out in the presence of 400 ppm of total active ingredient content based on the total mass of the solution/suspension of a mixture according to the invention of a crystallization additive and of an antifoam and of an amount of potassium hydrogen carbonate corresponding to the potassium ion concentration given in the table. The mixture according to the invention of a crystallization additive and of an antifoam consisted of an aqueous solution of 6.1% by weight of silicone oil with a kinematic viscosity of 1000 mm²/s (AK 1000, Wacker-Chemie GmbH), 0.25% by weight of hydrophobicized silica (Sipernat D10, Evonik Degussa GmbH), 2.6% by weight of a polyethoxylated fatty acid mixture (Intrasol® FS 18/90/7, Ashland Deutschland GmbH), 3.7% by weight of a polyethoxylated fatty alcohol mixture (2.35% by weight of Marlipal®, Sasol Germany GmbH, 1.35% by weight of Brij C2, Croda Chemicals Europe) and 5.1% by weight of a fatty alcohol sulphate (Sulfopon® 1218 G, Oleochemicals) according to the formula:

$$C_nH_{2n+1}-O-SO_3Na,$$

where n=12 to 18. The concentration of the pure crystallization additive was 117 ppm.

The bulk density of the precipitated methionine was determined after filtration and drying.

| $K^+$ concentration (g/l) | Bulk density (g/l) |
|---|---|
| 0 | 160 |
| 2 | 560 |
| 4 | 590 |
| 8 | 570 |
| 10 | 570 |
| 12 | 560 |
| 14 | 540 |

The addition of potassium ions accordingly leads to an improvement in the bulk density even at a low concentration of the fatty alcohol sulphate used as crystallization additive.

The invention claimed is:

1. A process for preparing D,L-methionine, the process comprising:
   feeding carbon dioxide to an aqueous potassium methioninate solution obtained by hydrolysis of 5-(2-methylmercaptoethyl)hydantoin, thereby precipitating out crude methionine, and
   purifying an aqueous solution of a separated-off crude methionine
   by recrystallization from a solution comprising potassium ions and a crystallization additive;
   wherein the recrystallization takes place by introducing a 60 to 110° C.-hot methionine solution into a 35 to 80° C.-warm methionine suspension, wherein a temperature of the warm methionine suspension is lower than a temperature of the introduced hot methionine solution, wherein a temperature of a mixture formed of the hot methionine solution and the warm methionine suspension is maintained between 35 and 80° C. during the introduction; and
   wherein the crystallization additive is a polyethoxylated sorbitan stearate.

2. The process of claim 1, wherein the polyethoxylated sorbitan stearate is a polyethoxylated sorbitan tristearate of the formula:

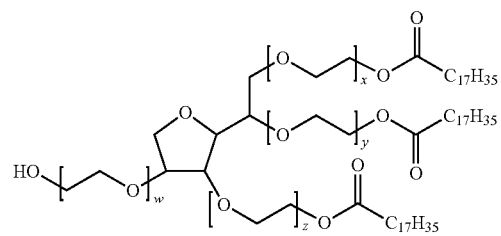

wherein w+x+y+z=20.

3. The process of claim 1, wherein a concentration of the crystallization additive in the solution from which the recrystallization takes place is at least 50 ppm based on the total mass of the solution and/or suspension.

4. The process of claim 1, wherein the solution from which the recrystallization takes place additionally comprises an antifoam.

5. The process of claim 4, wherein the antifoam comprises silicone oil.

6. The process of claim 1, wherein a potassium ion concentration in the solution from which the recrystallization takes places is from 1 to 30 g/kg.

7. The process of claim 1, wherein a potassium ion concentration in the solution from which the recrystallization takes place is 5 to 10 g/kg.

8. The process of claim 1, wherein the recrystallization takes place by introducing an 85 to 110° C-hot crude methionine solution into a 35 to 60° C.-warm methionine suspension, wherein a temperature of the mixture is kept constant between 35 and 60° C.

9. The process of claim 1, wherein the recrystallization is carried out in two stages, wherein in the first recrystallization stage, an 85 to 110° C.-hot crude methionine solution is introduced into a 60 to 80° C-warm methionine suspension, thereby forming a first mixture, wherein a temperature of the first mixture is kept constant between 60 and 80° C. and wherein a 60 to 80° C-warm methionine suspension obtained in the first recrystallization stage is introduced into a 35 to 60° C-warm methionine suspension in the second recrystallization stage, wherein a temperature of a mixture obtained in the second recrystallization stage is kept constant between 35 and 60° C.

10. The process of claim 1, wherein the recrystallization takes place by vacuum crystallization, wherein the recrystallization is carried out in two stages, and wherein a pressure in the first recrystallization stage is from 100 to 1000 mbar and from 35 to 200 mbar in the second recrystallization stage.

11. The process of claim 10, wherein in addition to the first and second recrystallization stages, the process comprises further recrystallization stages, and a part of the methionine suspension is removed from the first and/or at least one of the other recrystallization stages and is returned via a circulation circuit, wherein a temperature of a methionine suspension in the circulation circuit is increased by 6 to 12° C.

12. The process of claim 1, wherein the process comprises further recrystallization stages, and a part of the methionine suspension is removed from a first and/or at least one of the other recrystallization stages and is returned via a circulation circuit, wherein a temperature of a methionine suspension in the circulation circuit is increased by 6 to 12° C.

* * * * *